(12) United States Patent
Mueller

(10) Patent No.: US 9,493,731 B2
(45) Date of Patent: Nov. 15, 2016

(54) SOLUBLE TABLET, CONTAINING ABRASIVE MEDIA

(75) Inventor: Daniel Mueller, Burgstall (IT)

(73) Assignee: Dental Care Innovation GmbH, Nuremberg (DE)

( * ) Notice: Subject to any disclaimer, the term of this patent is extended or adjusted under 35 U.S.C. 154(b) by 0 days.

(21) Appl. No.: 13/520,762

(22) PCT Filed: Jun. 10, 2011

(86) PCT No.: PCT/IB2011/001327
§ 371 (c)(1),
(2), (4) Date: Jul. 5, 2012

(87) PCT Pub. No.: WO2012/069895
PCT Pub. Date: May 31, 2012

(65) Prior Publication Data
US 2013/0216595 A1    Aug. 22, 2013

(30) Foreign Application Priority Data

Nov. 12, 2010 (DE) .......... 10 2010 051 226

(51) Int. Cl.
B08B 7/00 (2006.01)
A61K 8/02 (2006.01)
C11D 17/00 (2006.01)
C11D 3/37 (2006.01)
C11D 7/20 (2006.01)

(52) U.S. Cl.
CPC ......... *C11D 17/0047* (2013.01); *A61K 8/0216* (2013.01); *C11D 3/3776* (2013.01); *C11D 7/20* (2013.01); *C11D 17/0073* (2013.01)

(58) Field of Classification Search
USPC .............................................. 424/401; 134/7
See application file for complete search history.

(56) References Cited

U.S. PATENT DOCUMENTS

| | | | |
|---|---|---|---|
| 5,506,248 A | 4/1996 | Nikfar et al. | |
| 6,245,732 B1 | 6/2001 | Gallon et al. | |
| 6,329,334 B1 * | 12/2001 | Bertleff et al. | 510/445 |
| 6,605,583 B1 | 8/2003 | Gorlin | |
| 2002/0122823 A1 | 9/2002 | Bunick et al. | |
| 2005/0214388 A1 | 9/2005 | Gorham et al. | |
| 2008/0170991 A1 * | 7/2008 | Shi et al. | 424/1.69 |
| 2008/0255498 A1 * | 10/2008 | Houle | 604/20 |
| 2008/0312168 A1 * | 12/2008 | Pilgaonkar et al. | 514/29 |
| 2009/0186081 A1 | 7/2009 | Holm et al. | |
| 2010/0330013 A1 | 12/2010 | O'Connell et al. | |

FOREIGN PATENT DOCUMENTS

| | | |
|---|---|---|
| AT | 337645 B | 7/1977 |
| AU | 604721 B2 | 1/1991 |
| DE | 102006021401 A1 | 12/2007 |
| DE | 69839342 T2 | 6/2009 |
| EP | 0002293 A1 | 6/1979 |
| EP | 0522766 A2 | 1/1993 |
| EP | 0673644 A1 | 9/1995 |
| EP | 0716144 A2 | 6/1996 |
| EP | 0812808 A1 | 12/1997 |
| EP | 0846756 A1 | 6/1998 |
| EP | 1048719 A1 | 11/2002 |
| EP | 1202663 B1 | 2/2003 |
| EP | 1371719 A1 | 12/2003 |
| EP | 1375636 A1 | 1/2004 |
| EP | 1382668 A1 | 1/2004 |
| EP | 1405900 A1 | 4/2004 |
| EP | 1405901 A1 | 4/2004 |
| EP | 1405902 A1 | 4/2004 |
| EP | 1418224 A1 | 5/2004 |
| EP | 1144585 B1 | 3/2005 |
| EP | 1533427 A1 | 5/2005 |
| EP | 1669438 A1 | 6/2006 |
| GB | 989683 | 4/1965 |
| GB | 1423536 | 2/1976 |
| WO | 9313658 A1 | 7/1993 |
| WO | 9518215 A1 | 7/1995 |
| WO | 9800467 A1 | 1/1998 |
| WO | 9831298 A1 | 7/1998 |
| WO | 9854284 A1 | 12/1998 |
| WO | 9940171 A1 | 8/1999 |
| WO | 0017311 A1 | 3/2000 |
| WO | 0058435 A1 | 10/2000 |
| WO | 0198448 A1 | 12/2001 |
| WO | 03104380 A1 | 12/2003 |
| WO | 2010077468 A1 | 7/2010 |

OTHER PUBLICATIONS

International Search Report in corresponding PCT/IB2011/001327 (four pages).

* cited by examiner

*Primary Examiner* — Adam C Milligan
(74) *Attorney, Agent, or Firm* — Hooker & Habib, P.C.

(57) ABSTRACT

In order to obtain steady erosion from soluble tablets and particularly constant dispersion of contained abrasive media, the employment of magnesium oxide and transverse interlaced polyvinylpyrrolidone (PVP) in defined layers and the admixing of randomly scattered silicic acids is suggested.

8 Claims, 1 Drawing Sheet

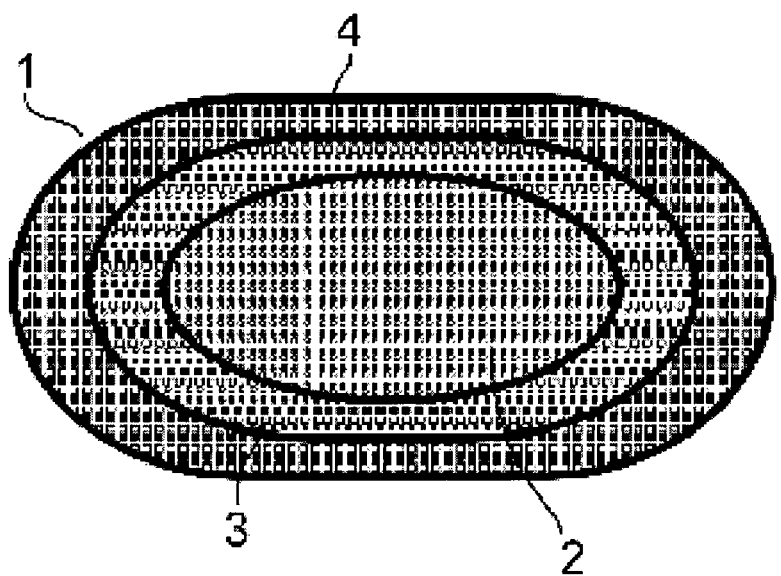

SOLUBLE TABLET, CONTAINING ABRASIVE MEDIA

FIELD OF THE INVENTION

The invention relates to soluble tablets, in particular those of cleaning agents with abrasive particles, and their constant dissolution in a stream of water or other solvents.

BACKGROUND OF THE INVENTION

For applications in cleaning equipment with a water jets, it is common to apply tablets containing the cleaning agent, to be dissolved in the supplied rinsing water.

In comparison to powdered additives these are simpler to batch and handle and have the advantage of a compact structure, which is favorable for storage and transport.

However, a frequent problem with the use of tablets is a too small decay and release speed, which prevents sufficiently fast release of the active ingredients in the cleaning medium, particularly at the end of the procedure.

One reason for this is, that in production of sufficiently break-proof tablets high pressing powers use to be applied, which lead to a very compact structure.

The other one is, that due to decay of the surface area the dissolution of particle mass declines, so that the concentration of active agents in the solvent varies from high at the beginning to low at the end, thus forcing to convey an otherwise useless amount of water or solvent only to rinse out the rest of the tablet—which otherwise needs to be tediously removed.

PRIOR ART

From prior art quite a few approaches are known for improvement of the solubility of tablets. One of it is adding soluble compactors, e.g. polyethylene glycols, usually with 2 to approximately 6% by weight into the tablet composition, that replaces the application of high pressing power.

Another method is the admixture of macerating structure-breakers, usually in quantities from 10 to approximately 30% by weight to the substance, as e.g. micro-crystalline cellulose, saponite or macerating synthetic polymers.

However, these usually are additives, which do not make any contribution to the intended cleaning effect of the tablet.

Furthermore a well-known possibility of accelerating the decay of tablets in water would be adding substances, that release gases when wetted, e.g. combinations of soluble carbonates and solid acids. The application of this principle on tablets with cleaning agents are found in patent applications DE 198 47 283 A1, WO 98/0467 A1, WO 98/5 42 84 A1 and WO 00/5 84 35 A1, together with some older literature quoted therein.

Generally in tablet production the powdered ingredients are mixed and then pressed in molds to form tablets, whereas in some cases it had been seen favorable, to convert several of the ingredients into granulates first, as disclosed in DE 198 47 283 A1 and WO 00 58435, and then inject it together with the remaining ingredients into the tablet mold.

Another procedure refers to implementing cleaning tablets in a way, that a firm and smooth phase covers a full phase, as disclosed in EP 1.371.719, EP 1.405.900, EP 1.383.668, EP 1.375.636, EP 1.405.901, EP 1.405.902, and EP 1.418.224 as well as WO 03/10 43 80.

However, as DE 60 2005 002 917 T2 and EP 1.669.438 B1 indicates, this requires separate manufacturing of the smooth phase and the full phase, followed by assembly and packing. This makes the manufacturing of these cleaning tablets intricate, time-consuming and expensive.

Opposite to this, DE 60 2005 002 917 T2 suggests the supply of a core compound of consolidated particle material, followed by firmly encasing it with an outer shell and then to inject a fluid composition into the form to build up the second phase; and later to remove the shell after solidification of the second range, if required.

However, it remains questionable whether this procedure of the production of two-phase tablets is not at least just as intricate as the aforementioned ones.

Further to prior art the four following intellectual property rights may be considered:

1.) European patent application EP 0.812.808 A1 describes water softening tablets, which additionally to other auxiliary materials contain a polyfunctional carbonic acid and/or a salt of it, 10 to 70% of weight from a mixture of citric acid and trisodium citrate, 15 to 45% of weight of carbonate and/or bicarbonate, 1 to 6% bonding agent, 2 to 19% polymers, 0 to 45% stratified silicates and/or alkali metal silicate, 0 to 15% solubilizing agent, as well as 0 to 5% precipitation inhibitors, which should result in a fast and constant dissolution.

2.) European patent application EP 0.673.644 A1 discloses a procedure for the production of shower granulates, which can contain citric acid and trisodium citrate, wherein the granulation is effected under aqueous conditions: firstly atomized water or a atomized aqueous solution is sprayed onto the granulated mixture, in order to evaporate the water, short time thereafter this is repeated to an extent of just avoiding an uncontrollable foaming reaction. On renewed contact with water the tablet should dissolve steadily and quickly.

3.) German utility patent DE 297 23 656 U1 discloses a molded detergent structure, which contains a builder substance and at least one break-open agent, present in co-granulated shape to form in the molded article. The granulates, which must be present in defined particle size, contains at least 20% of the break-open agent for to achieve an appropriate effect.

4.) European patent application EP 0.628.627 A1 describes a water-solubly, water-demineralizing consistency in form of a tablet, wherein 60-98% is a combination of a) citric acid and b) a polymer as softener in a weight ratio of and from 70:30 to 50:50, preferably 65:35 to 55:45, (B) 0.5-6% polyethylene glycol as well as (C) 0-38% other auxiliary materials.

However, since the effect refers to water softening as a condition for machine laundry, this procedure is unsuitable for water blasting.

Moreover, EP 1.144.585 B1/DE 600 19 084 T2 (to Procter & Gamble) proposes a composition, in which mixtures of polymeric degradation means of a certain particle size distribution in combination with certain water-soluble hydrated salts are particularly favorable for improving the dissolution behavior of cleaning agent tablets. The tablet described there contains one or more phases, whereby at least one consists of a compressed particle, comprising:

a) a polymer dismantling means, selected from starch, cellulose and derivatives thereof, alginates, sugars, polyvinylpyrolidones, hygroscopically swelling clays and mixtures of it, with a such particle size distribution that at least 90% of it consist of a particle size below 0.3 mm and at least 30% of it a particle size below 0.2 mm; and b) a water-soluble hydrated salt with a solubility in distilled water of at least 25 g/100 g at 25° C., wherein the cleaning agent tablets always contain 0.5% to 10% polymeric dismantling means and water-soluble hydrated salts.

The polymeric dismantling means preferably comes in a particle size distribution in which at least 90% of it is below 0.25 mm and at least 50% of it has a particle size below 0.2 mm. Moreover, preferred dismantling means have such a particle size distribution, that at least 90% of it are above 0.05 mm, preferably above 0.075 mm.

In summary, tablet dismantling means as to prior art can be described as materials, which increase the tablet dissolving speed in a cleaning medium. Suitable polymeric dismantling means therefore include polymers, which macerate on contact with water, as well as those, which facilitate water intrusion and release by forming channels inside the tablet.

Examples of suitable dismantling means include materials on starch and cellulose basis. Thereof in P&G products Vivapur and in particular Vivapur G200 (a micro-crystalline cellulose with an average particle size of approximately 0.18 mm) is used for increased dissolving speed and tablet firmness, as well as for longer storage time. The hydrated salt contained in it is preferably water soluble to an extent of at least 40 g/100 g, but preferentially to 60 g/100 g of distilled water at 25° C.

Furthermore one of the water-soluble hydrated salts preferably has a fusion point within the range of 30° C. to 75° C. The water-soluble hydrated salts have been selected from hydrates of sodium acetate, sodium metaborate, sodium orthophosphate, sodium 2-hydrogen phosphate, 2-sodium hydraulic phosphate, etc. and its mixtures.

For to produce break resistant tablets with high decay and release speed at low pressing powers, it is further state of the art, to transform the ingredients of the tablet before pressing into more solid granulates by mixture granulation, as suggested in DE 10123621 B4.

Another method to make tablets break resistant and to deliver their ingredients media in an controlled rinsing-off stream is taught in DE 696 37 030 T2/EP 0.846.756 B1 by Procter & Gamble using cladding layers.

Although tablets without coating are effective for use, usually they lack the necessary surface hardness to resist abrasion, which happens on normal production, packing and handling. Numerous procedures for the coating of tablets were suggested, and many of these were suggested for cleaning agent tablets. However, all these procedures inherit certain disadvantages:

GB-A-0 989.683, published on 22 Apr. 1965, discloses a procedure for making detergent particulates of tensides and inorganic salts by spraying water-soluble silicates onto detergent particles and pressing this into a tablet, which therefrom retains its form.

Finally, a film-building and easily water-soluble organic polymer (for example polyvinyl alcohol) is applied for coating, to prevent abrasion and inadvertent fracture.

EP-A-0.002.293, published on 13 Jun. 1979, discloses a tablet coating, which consists of hydrated salts, like acetate, metaborate, orthophosphate, tartrate and sulfate.

EP-A-0.716.144, published on 12 Jun. 1996, reveals also cleaning agent tablets with water-soluble coatings, which can be organic polymers.

WO 95 182 15, published on 6 Jul. 1995, makes water-insoluble coatings available for firmly casted tablets. These are provided with hydrophobic coatings, including paraffin wax, fatty acid, fatty acid amides and polyethylene glycol.

One disadvantage in these propositions is, that a coating which is thick and strong enough to withstand abrasion, will also be slow in breaking open and dissolving on application.

P&G therefore offer a solution in U.S. Pat. No. 6,245,732, in which tablets have a core, formed by compression of a particulate material (that comprise tensides and detergent builders) with a hard, but thin coating. The coating is mechanically broken when closing particular rinsing-out compartments in washing machines, so that the soft core lies open, which then breaks apart fast and easily, thus setting the active components free into the suds.

The goal is a tablet, which decomposes completely, particularly in dilutions containing alkaline and strong tensides—as in washing liquors.

Disregard the fact, that this would only work with particular machinery, a composition which only dissolves in a detergent liquor, is inapt to tablets for e.g. water jets.

On the other hand, DE 697 30 599 T2 and EP-A-0.002.293 (as well from P&G) lists the following other prior art, criticizing that these cannot be washed out without leaving residues:

Thus EP-A-0.716.144, published on 12 Jun. 1996, discloses cleaning agent tablets with water-soluble coatings, which can be organic polymers. It is indicated that the tablets according to that invention achieve a diametric breaking resistance of at least 5 kPa and a high dissolution speed, that was measured by application of a metal net.

EP-A-0.522.766, published on 13 Jan. 1993, discloses a tablet from consolidated particulate cleaning composition, in which the tablet—or a discrete part of it—essentially consists of a matrix of particles, which are free from particles of less than 200 micrometers size. Particles of the cleaning-active composition and detergent builders are individually coated with actively decomposing substance with the ability to break open when immersing the tablet in water.

The advantage of latter proposals is that they refer to a purposeful decay of the tablet in water alone, not only in alkaline solutions. However they do not contain abrasive components, the controlled release of which is the task of this invention and which would not so easily be integrated without interfering with these functions.

Furthermore a set of proposals is known, which were developed in the detergent industry, that refer to a "controlled release" of active substances from a tablet:

So EP 957.159 A1 (from Chimiotechnic) discloses a cleaning agent tablet, in which builders and whiteners are in separate phases and the different dissolution speeds of these phases result in a temporally shifted release of their ingredients.

Also a temporally retarded release of tensides from coated granulates and the use of these granulates in washing and cleaning agents is known from P&G's WO 00/17311 A1.

A multi-phase tablet, containing wash- and cleaning agents in different phases is also proposed by Hindustan Lever Limited in WO 99/40171 A1. The fabric softeners here are said to be formulated to have longer disintegration time so to be released with a timely offset.

Closely related to this prior art is EP 1.048.719 A1, wherein the necessary timely different activation of ingredients are taught to be managed by separating it in different regions and phases.

In all these disclosures referring to controlled release of active ingredients from tablets is achieved through selected carrier or encapsulating substances with characteristic dissolution profiles in water based media.

However, disregard of their dissolution inhibiting characteristics, these substances inherit no cleaning effect, but contain a substantial volume and thus part of the weight and cost of the tablets.

In contrast, DE 199 34 704 A1 and DE 10130 762 C2 offer a general approach for dosing detergents in form of a monolithic preform. Manual dosing control is here provided by integrated rated breakpoints—whereas it may be questionable, how to manage this within a running process.

Referring to cleaning applications with blast media, a major disadvantage of afore cited methods is the mostly deficient dissolution of the tablets, if there is only a dosed amount of water to rinse it out—respectively, if a constant stream of media with a constant concentration of agents is required and the system has to be shut off after its decline.

In order to avoid this, such tablets may be designed in several layers, which dissolve more quickly as closer they are to the center.

Thus GB 01/02773/DE 601 01 482 T2/EP 1.202 663 B1 and WO 01/098488 describe tablets, now available in the trade, which contain two or more layers from a compressed, granular or powdery composition and a tablet, which contains a cavity, filled with a composition, which differs from the main phase—for example a dishwasher tablet, which basically is a two-layer tablet joint with a third composition pressed in to form a ball, which is punched into the upper surface of the main tablet.

This ball shows a color, different from the other two layers and contains a dissolution activator, whereas the two other layers are covered by soft inhibitors, so that the ingredients of the ball are dissolved in advance.

The two shells of the tablet are formed by compacting particulate material. The cavity is formed by an upper mold of suitable convex shape, wherefrom the dish sections below is heavier compressed than the top of the tablet, which is more gently pressed with a concave mould thereon—thus providing a different density.

An advanced design for "controlled release" by the mechanical structure of layers when forming the tablet is also given in DE 199 22 578 C2:

These tablets are manufactured in similar molds like those for single layer tablets, however with some modifications. In case of a two-layered tablet usually primarily a first mixture is filled with a first composition into a mold and squeezed with a first pressure.

Subsequently, a second mixture with a second, different composition is filled on the squeezed first layer in the mold and concluding pressing is accomplished with a second, usually higher pressure.

However, for tablets with at least two layers the problem arises, that the connection between the individual layers must be sufficiently stable, in order to prevent a separation of the layers from each other on storage and transport.

The causes for this maybe various—as e.g. different volumetric expansion of the individual layers, reactions at the boundary surfaces, etc. Consequently it is necessary to adjust the compositions of the individual layers correspondingly and apply exactly rated force when pressing these together.

Therefore, development and production of stable multi-level tablets obviously are time consuming and costly as well as sensitively dependant of correctly keeping internal and external parameters during the process.

This is as well detailed in DE 199 22 578 C2, which describes the procedure for the production of such a tablet with at least one first and a second layer, that covers the following steps:

a) Inserting a first measured quantity of a first particulate composition into a negative mold of a tablet press;

b) Pressing of the first measured quantity with a first pressing power by means of a positive-press stamp in order to manufacture a first pressed layer, which in its surface shows indentations that correspond on the press stamp;

c) Inserting a second rated quantity of a second particulate composition onto the first pressed layer into the recess of the first pressing; and d) pressing of the second measured quantity with a secondly rated pressing power by means of press stamp, for to produce a second pressed layer with an appropriate recess in its upper surface, to finish the product with c) a covering layer thereafter.

For special products these procedures for the production at least a further layer the steps (c) and (d) might be repeated.

This may prove that the manufacture of multi layer tablets is not only intricate because extensive processing steps must be made and precautions taken in order to accomplish the dissolution in phases as desired.

Moreover, a completely separated release of active materials in timely sequences cannot always be accomplished with these methods due to their complex structure, where a possible timely decay of single ingredients as well as different water hardness and minerals contained might spoil the differentiated effects.

Furthermore, particularly in case of controlled release of abrasive blast grain—which themselves cannot dissolve— in a stream of water, conglomerations may appear after loss of the chemical connection to binders and aids, which can lead to blockage of hoses and jet nozzles.

Problem to be Solved

It therefore is the object of the present invention, to provide a tablet with abrasive blast grains, the composition of which provides constant dissolution unto the end, while avoiding substances, that do not contribute to the main intended effect and agglomerations and remainders that might clog ports and hoses or nozzles.

The object of the invention is basically achieved by a forming a tablet from magnesium oxide as abrasive blast grain.

However, highly dosed magnesium oxide in water is prone to lump formation, which again could result in clogging nozzles of radiation devices. Therefore on one hand the use of caustically burned magnesite needs to be avoided, which is particularly susceptible to it, when recovered from calcining magnesium carbonate (magnesite) from natural sources.

But even avoiding this, MgO can only be applied in limited quantities as abrasive media, if constant and complete dissolution of the tablets is to be achieved.

Inventive Step

The inventive step therefore is to apply a further blast grain, which can simultaneously be used for controlled breaking up the structure by water absorption, furthermore to find combinations of ingredients, that could be processed together to make a multi-stage effect, without needing intricate means of binding it mechanically by pressing together different layers or using chemical binders etc.

This was found in a particular combination of MgO and transvers interlaced (that is, cross-linked) polyvinylpyrrolidone (PVP) which itself is used in tablets for multiple functions.

PVP appears as colorless crystals in a sodium chloride structure and is recovered by thermal conversion of other magnesium compounds. This is often applied in the building and food chemistry, e.g. as acid modulator or parting agents.

Simple "linear" PVP is a hygroscopic, amorphous powder, which quickly dissolves in water. While its basic material vinylpyrrolidone is rated carcinogen in category 3, the transverse interlaced polymer however is considered to be harmless to humans and therefore often used in pharmaceutics. Therefore, named Crospovidon, it is rated in the EU under En AB 6.0.

It is certified in the European Union as additive with code E 530 without maximum quantitative restriction (quantity satis) for food and is therefore—contrary to some the aforementioned components of cleaning tablets—also applicable to means for dental care.

Due to its macerating properties PVP is here applied to dissolute compressed tablets and simultaneously to work as a gently abrasive blast grain.

In a preferred embodiment of this invention the optimum distribution changes gradually from the external layer containing 80% MgO and 10% PVP to 40% MgO and 50% PVP and in the center, which—due to different volume in the outer and inner radii totals to 60% MGO and 30% PVP, while the remaining 10% of the components may consist of bonding agents and foarming means, as e.g. magnesium stearate and useful additives to the cleaning process, as is highly dispersed silicic acids, which enhance the flowability.

The high concentration of PVP and additives in the center provoke faster dissolution of the tablet and less remainder in the final phase, without therefore applying a bigger quantity of water, which otherwise would reduce the concentration of active substances when approaching the final phase.

The technical advantage of the this combination is, that the multistage release effect is achieved without complicated production methods, since these components adhere due to week Van-der-Waal forces.

Therefore it proved to be sufficient to fill the components successively into two halves of a press mould before grouting it together, whereby avoiding complicated manufacturing processes, as specified for multi-phase-tablets, e.g. in DE 199 225 78 page 1 line 36.

DESCRIPTION OF THE INVENTION IN A DRAWING

The structure of a tablet according to this invention is represented in FIG. 1, which shows the structure of the tablet 1 in a cross section view.

The core 2, which contains 50% PVP and to 40% MgO particles, whereas a transition layer 3 comprises a relationship of 50% MgO and 40% PVP and the outside layer 4 consists of 60% MgO and only 30% of PVP.

| List of Cited Patents | | | | | |
|---|---|---|---|---|---|
| In the Order of Citations | | | In Alphabetical Order | | |
| No. | view PAGE | LINE No. | No. | view PAGE | LINE No. |
| DE 198 47 283 A1 | 3 | 4 | DE 10330 762 C2 | 7 | 13 |
| WO 98/0467 A1 | 3 | 4 | DE 198 47 283 A1 | 3 | 4 |
| WO 98/54284 A! | 3 | 4 | DE 19847 283 A1 | 3 | 9 |
| WO 00/58435 | 3 | 4 | DE 199 22 578 C2 | 7 | 42 |
| DE 19847 283 A1 | 3 | 9 | DE 199 22 578 C2 | 8 | 21 |
| WO 00 584 35 | 3 | 9 | DE 199 34 704 A1 | 7 | 13 |
| EP 1.371.719 | 3 | 13 | DE 297 23 656 U1 | 4 | 1 |
| EP 1.405-900 | 3 | 13 | DE 60 2005 002 917 T2 | 3 | 16, 19 |
| EP 1.383.668 | 3 | 13 | DE 600 19 084 T2 | 4 | 13 |
| EP 1.375.636 | 3 | 14 | DE 601 01 482 T2 | 7 | 27 |
| EP 1.405.901 | 3 | 14 | DE 696 37 030 T2 | 5 | 11 |
| EP 1.405.902 | 3 | 14 | DE 697 30 599 T2 | 6 | 9 |
| EP 1.418.224 | 3 | 14 | EP 0.628.627 A1 | 4 | 6 |
| WO 03/104380 | 3 | 14 | EP 0.673.644 A1 | 3 | 37 |
| DE 60 2005 002 917 T2 | 3 | 16, 19 | EP 0.812.808 A1 | 3 | 30 |
| EP1.669.438 B1 | 3 | 16 | EP 0.846.756 B1 | 5 | 11 |
| EP 0.812.808 A1 | 3 | 30 | EP 1 048 719 A1 | 7 | 1 |
| EP 0.673.644 A1 | 3 | 37 | EP 1.144.585 B! | 4 | 13 |
| DE 297 23 656 U1 | 4 | 1 | EP 1.371.719 | 3 | 13 |
| EP 0.628.627 A1 | 4 | 6 | EP 1.375.636 | 3 | 14 |
| EP 1.144,585 B! | 4 | 13 | EP 1.383.668 | 3 | 13 |
| DE 600 19 084 T2 | 4 | 13 | EP 1.405-900 | 3 | 13 |
| DE 696 37 030 T2 | 5 | 11 | EP 1.405.901 | 3 | 14 |
| EP 0.846.756 B1 | 5 | 11 | EP 1.405.902 | 3 | 14 |
| GB-A-0 989.683 | 5 | 21 | EP 1.418.224 | 3 | 14 |
| EP-A-0 002.293 | 5 | 27 | EP 1202 663 B1 | 7 | 27 |
| EP-A-0 716.144 | 5 | 30 | EP 957.159 A1 | 6 | 32 |
| WO 95 18 215 | 5 | 33 | EP-A-0 002.293 | 5 | 27 |
| U.S. Pat. No. 6,245,732 | 5 | 40 | EP-A-0 002.293 | 6 | 9 |
| DE 697 30 599 T2 | 6 | 9 | EP-A-0 716.144 | 5 | 30 |
| EP-A-0 002.293 | 6 | 9 | EP-A-0 716.144 | 6 | 12 |
| EP-A-0 716.144 | 6 | 12 | EP-A-0522.766 | 6 | 17 |
| EP-A-0522.766 | 6 | 17 | EP1.669.438 B1 | 3 | 16 |
| EP 957.159 A1 | 6 | 32 | GB 01/02773/ | 7 | 27 |
| WO 00/17311 A1 | 6 | 36 | GB-A-0 989.683 | 5 | 21 |
| WO 99/40171 A1 | 6 | 40 | U.S. Pat. No. 6,245,732 | 5 | 40 |
| EP 1 048 719 A1 | 7 | 1 | WO 00 584 35 | 3 | 9 |
| DE 199 34 704 A1 | 7 | 13 | WO 00/17311 A1 | 6 | 36 |
| DE 10330 762 C2 | 7 | 13 | WO 00/58435 | 3 | 4 |
| GB 01/02773/ | 7 | 27 | WO 03/104380 | 3 | 14 |
| DE 601 01 482 T2 | 7 | 27 | WO 95 18 215 | 5 | 33 |

-continued

List of Cited Patents

| | In the Order of Citations | | | In Alphabetical Order | |
|---|---|---|---|---|---|
| No. | view PAGE | LINE No. | No. | view PAGE | LINE No. |
| EP 1202 663 B1 | 7 | 27 | WO 98/0467 A1 | 3 | 4 |
| DE 199 22 578 C2 | 7 | 42 | WO 98/54284 A! | 3 | 4 |
| DE 199 22 578 C2 | 8 | 21 | WO 99/40171 A1 | 6 | 40 |

What is claimed is:

1. A method for cleaning a surface of a tooth, the method comprising the steps of:
    (a) continuously flowing a stream of water past a water-soluble tablet, the tablet comprising magnesium oxide (MgO) and cross-linked polyvinylpyrrolidone (PVP) arranged in a plurality of concentric layers, each layer comprising MgO grains and PVP grains, wherein the relationship of the MgO grains and the PVP grains is different in each layer;
    (b) allowing the stream of water flowing past the tablet to wet the tablet;
    (c) dissolving the wetted tablet in the stream of water flowing past the tablet, the wetted tablet dispersing MgO grains and PVP grains into the stream of water flowing past the wetted tablet, the MgO grains and the PVP grains dispersed into the water being dental abrasives capable of cleaning a tooth surface by abrasive action;
    (d) while the wetted tablet is dissolving, directing the stream of water containing the MgO grains and the PVP grains from the dissolving tablet towards the tooth surface and impinging that flow of water against the tooth surface wherein the MgO grains and the PVP grains in the impinging water impinge against the surface of the tooth; and
    (e) cleaning the tooth surface at least in part by the abrasive action of the MgO grains and the abrasive action of the PVP grains both impinging against the tooth surface.

2. The method of claim 1 wherein the concentration of PVP in the water-soluble tablet increases from an external layer of the water-soluble tablet towards a center of the water-soluble tablet.

3. The method of claim 2 wherein the plurality of layers comprises a core layer surrounded by the other layers of said plurality of layers, the core layer comprising 35% to 45% MgO and 45% to 55% PVP.

4. The method of claim 2 wherein the plurality of layers includes an outer layer, the outer layer comprising 55% to 65% of MgO and 25% to 35% of PVP.

5. The method of claim 2 wherein each layer of the plurality of tablet layers is formed by pouring granulated MgO and granulated PVP into half moulds.

6. The method of claim 1 wherein the tablet comprises a hydrophobic material.

7. The method of claim 6 wherein the hydrophobic material comprises silicic acid.

8. The method of claim 1 comprising the step of: pouring granulated MgO and granulated PVP into half moulds to form the tablet.

* * * * *